United States Patent [19]

Mizuki

[11] Patent Number: 4,510,625
[45] Date of Patent: Apr. 16, 1985

[54] LIGHT-SHIELDING PROTECTIVE MASK

[76] Inventor: Nobuo Mizuki, 886-55 Hiratocho, Totsuka-ku, Yokohama City, Kanagawa Prefecture, Japan

[21] Appl. No.: 313,645

[22] Filed: Oct. 22, 1981

[51] Int. Cl.³ .............................................. A61F 9/06
[52] U.S. Cl. .................................... 2/8; 200/DIG. 2; 200/61.58 R
[58] Field of Search .......... 2/8; 200/DIG. 2, 61.58 R; 362/104

[56] References Cited

U.S. PATENT DOCUMENTS

| | | | |
|---|---|---|---|
| 2,516,180 | 7/1950 | Brown | 200/DIG. 2 |
| 3,700,835 | 10/1972 | Rackson | 200/DIG. 2 X |
| 3,833,936 | 9/1974 | Lo Guidice | 2/8 |
| 4,059,830 | 11/1977 | Threadgill | 200/DIG. 2 X |

FOREIGN PATENT DOCUMENTS

| | | | |
|---|---|---|---|
| 455648 | 1/1928 | Fed. Rep. of Germany | 2/8 |
| 1193583 | 5/1965 | Fed. Rep. of Germany | 200/DIG. 2 |
| 39-10465 | 4/1964 | Japan | |
| 725166 | 3/1955 | United Kingdom | 2/8 |

Primary Examiner—Peter Nerbun
Attorney, Agent, or Firm—Lucas & Just

[57] ABSTRACT

A switch holder is made from a rubber or a plastic and has an endless ring-like form or an arcuate form cut at both ends to fit a finger of the worker who makes the welding. A switch having a small depression stroke is mounted on the periphery of the switch holder so as to be pressed by the flank of an adjacent finger. Thus, when the worker gripping a safety holder clamping a welding rod by his hand wearing the switch holder increases the gripping force, or when he intentionally increases the gripping force without holding anything, the push button is pressed by the flank of the adjacent finger. A protective mask body electrically connected to this switch accomodates a conversion means for converting the rotation of the shaft of a motor into a linear movement, and a light-shielding plate connected to the conversion means so as to move between a light shielding position where it covers the window of the mask body and a clearing position where it opens the window. The motor is started by the depression of the switch in advance to the generation of the arc to move the light-shielding plate to the shielding position to protect eyes of the worker. Upper and lower limit switches are provided to limit the upward and downward movement of the light-shielding plate.

5 Claims, 10 Drawing Figures

FIG.5
FIG.6
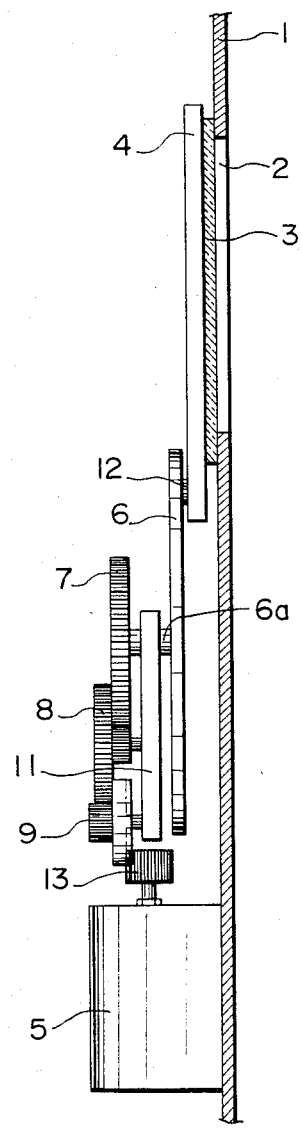
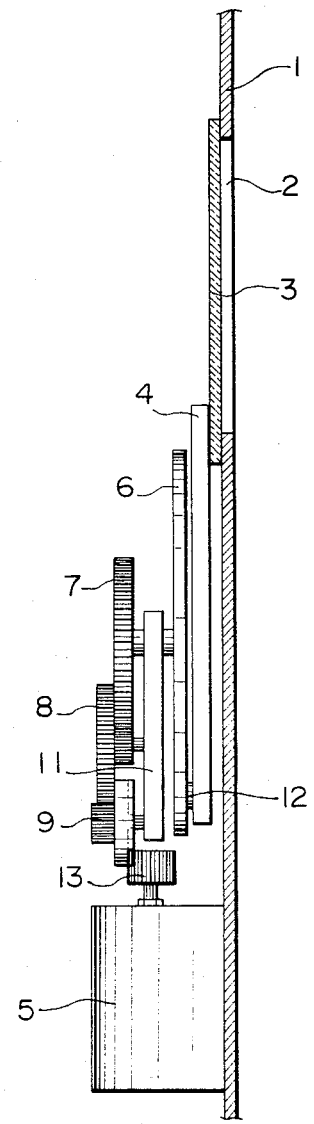

LIGHT-SHIELDING PROTECTIVE MASK

BACKGROUND OF THE INVENTION

The present invention relates to a light-shielding protective mask for protecting eyes and face skin of the worker from the arc light during welding.

Such an electrically controlled variable light transmission mask has been known as having a filter of variable light transmission coefficient and a controller adapted to change the light transmission coefficient upon detection of an arc light or arc current such that the light transmission coefficient is reduced when the arc light exixts and increased when there is no arc current. This kind of protective mask is advanategously permits observation of state of welding during suspension of the arc light without detaching the mask from the face to permit the worker to conduct the welding while checking the welding condition as required.

An example of this kind of mask hitherto proposed employs a liquid crystal cell driven by a driving circuit which is started upon detect of the arc light or the welding current by which the arc is generated. The reduction of light transmission coefficient, therefore, is commenced with a certain time lag (about 0.2 sec) to he generation of the arc. Therefore, within the period of this time lag, the strong light comes into eyes through the filter the light transmission coefficient of which has not been reduced yet.

This light, however, does not seriously damage eyes partly because the liquid crystal cell usually incorporates an ultraviolet ray absorption filter and partly because the time length of application of light is so large. However, this application of light makes the worker dizzy, so that the worker has to take a necessary precaution measure such as to close his eyes, avert his eyes away from the welding object and so forth, at least at the moment just before the start of welding. This seriously hinders the efficiency of the welding work in which the arc light goes on and off frequently.

The liquid crystal cell shows only a small range of change of light transmission coefficient. For instance, a liquid crystal having the minimum transmission coefficient of 0.002% has the maximum transmission coefficient of 3%. The worker, therefore, is obliged to inspect the minute portion of welded part under insufficient illumination.

It has been proposed also to reduce the light transmission coefficient just before the generation of arc by operating a foot switch on the floor. This, however, is not practical because it is quite troublesome to move the foot switch in accordance with the movement of the worker. This countermeasure, therefore, is not suitable when the welding has to be done over a wide range.

SUMMARY OF THE INVENTION

Accordingly, an object of the invention is to provide a light-shielding protective mask which is safe and easy to handle, wherein a light-shielding plate of a low light transmission coefficient is mounted on the window of the mask in such a manner as to be able to move up and down, thereby to permit a light-receiving surface of low light transmission coefficient in advance to the start of the arc light.

Another object of the invention is to provide a light-shielding protective mask of the type mentioned above, wherein the light-shielding plate is electrically driven to move up and down by a manipulation of a switch positioned near the worker's hand, thereby to eliminate erroneous operation due to the application of sunlight to make sure of the efficient outdoor welding operation.

Still another object of the invention is to provide a light-shielding protective mask in which the switch is manipulated by the pressing force exerted by the side of a finger which varies in accordance with the change in the gripping force, so that the light transmission coefficient can be controlled easily in close relation to the welding operation.

BRIEF DESCRIPTION OF THE DRAWINGS

FIG. 5 is a vertical sectional view taken along the line V—V of FIG. 4;

FIG. 6 is a vertical sectional view of the same portion as that shown in FIG. 5 in the state in which the light-shielding plate takes the lowermost position;

DESCRIPTION OF THE PREFERRED EMBODIMENTS

Figure 1:
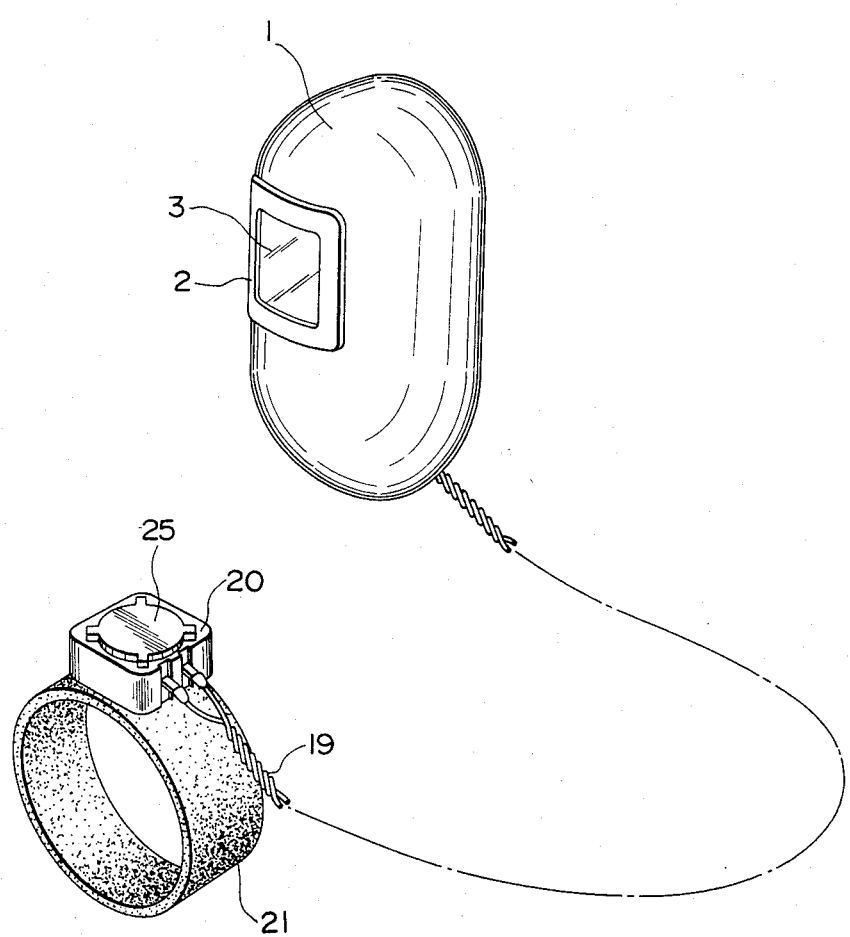
FIG. 1 is a perspective view of the body of a protective mask and a switch holder connected to the outer end of a lead wire extended from the mask body.
Figure 2:
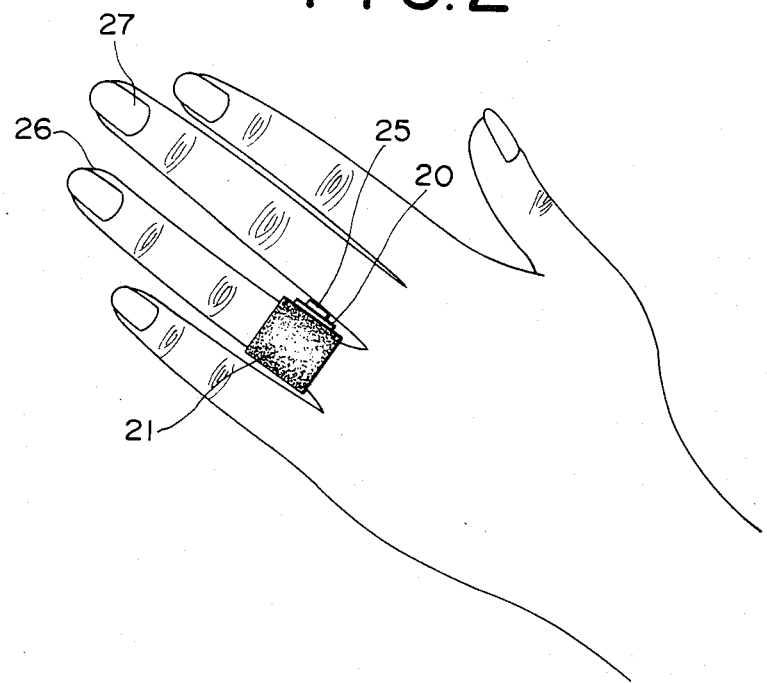
FIG. 2 is a perspective view of the back side of a hand wearing the switch holder on a finger.

Briefly, according to the invention, there is provided a light-shielding protective mask comprising a mask body having an window; means for forming a light incoming surface on the window; a ring-shaped switch holder adapted to fit a finger; and a switch having a small depression stroke and held by the switch holder in such a manner as to take a position between two adjacent fingers, the switch being electrically connected to the aforementioned means so that the switch is selectively manipulated by the pressure exerted between two fingers in accordance with the change in the gripping force by hand thereby to form the light incoming surface of the small light transmission coefficient on the window.

Preferred embodiments of the invention will be described hereinunder with reference to the accompanying drawings.

Referring to the drawings, a mask body 1 made from a plastic has a curvilinear wall genrally capable of covering the entire part of the worker's face. Although not shown, the mask body 1 is provided at its both sides with suitable means for rotatably securing the mask body 1 to a helmet. The mask body 1 has a window 2 opened in its front side and is covered by a filter 3 having a large light transmission coefficient. This filter 3, however, is not essential and may be omitted.

Figure 4:
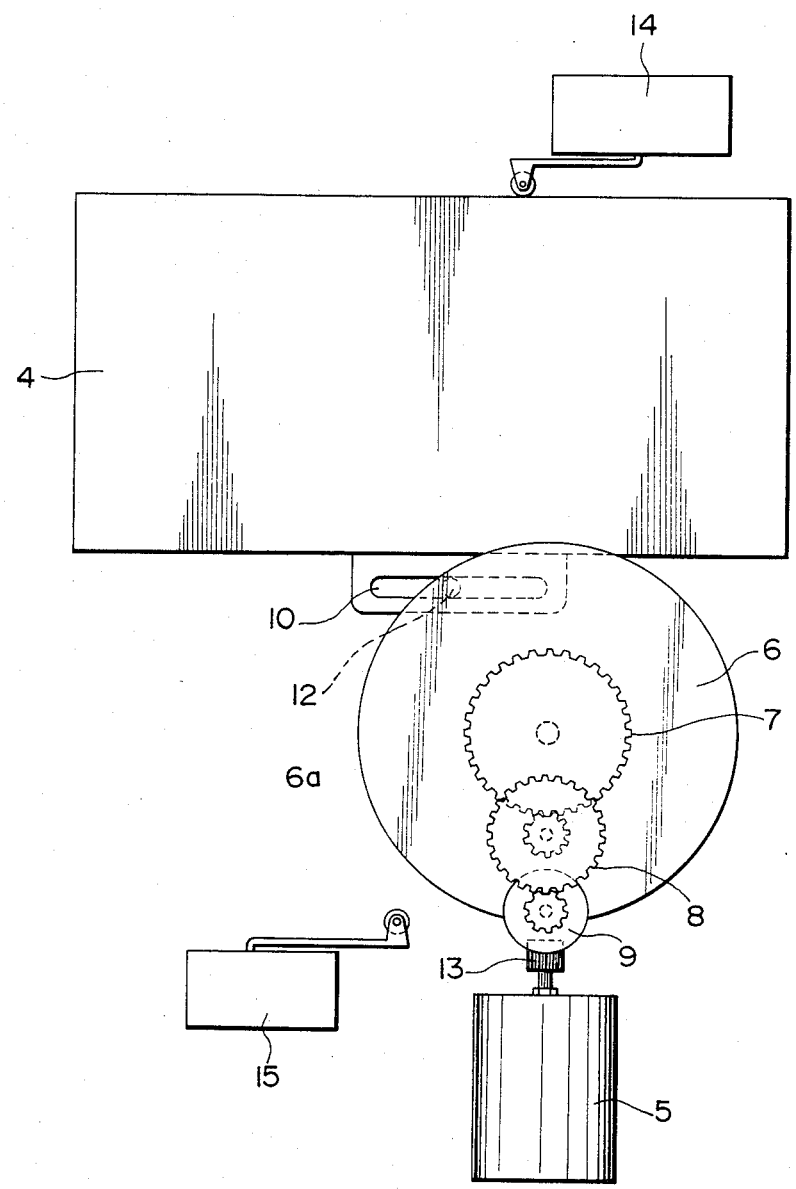
FIG. 4 is a schematic illustration of a mechanism for moving a light-shielding plate up and down, in the state in which the light-shielding plate takes the upper limit position.

A mechanism for moving a light-shielding plate 4 up and down is mounted inside the mask body 1. As will be seen from FIG. 4, this mechanism includes a motor 5, light-shielding plate 4, a rotary disc 6 and a reduction gear train 7,8,9 operatively connecting the light-shielding plate 4 to the motor 5.

The light-shielding plate 4 inherently has a low light transmission coefficient. The plate 4 has a size somewhat greater than the window 2 of the mask body 1 and is mounted inside the latter to close the whole part of the window 2. A guide groove 10 of a predetermined length is formed in the lower edge of the plate 4 to extend in the breadthwise direction of the latter. The guide groove 10, however, may be formed on the upper edge of the plate 4. The rotary disc 6 is mounted inside the light shielding plate 4 and secured to the stationary plate 11 by means of a rotor shaft 6a. A guide pin 12 is formed on the disc surface facing the guide groove 10 and is received by the latter. The arrangement is such that, as the rotary disc 6 rotates in one and the other directions, the guide pin 12 moves along an arcuate path and slides in the guide groove 10 thereby to swing the light-shielding plate 4 up and down.

One 7 of the gears of the gear train is unitarily secured to the outer end of the shaft 6a of the disc 6, while other gears 8,9 are supported rotatably by a stationary plate 11. The gear 9 meshes with a motor shaft pinion 13. The motor 5 is firmly secured to the inner side of the mask body 1.

Reference numerals 14 and 15 denote limit switches adapted to be contacted by the upper and lower edges of the light-shielding plate 4 when the latter 4 is moved to the uppermost and lowermost positions in accordance with the forward or backward rotation of the motor 5, thereby to stop further rotation of the motor 5.

Figure 7:
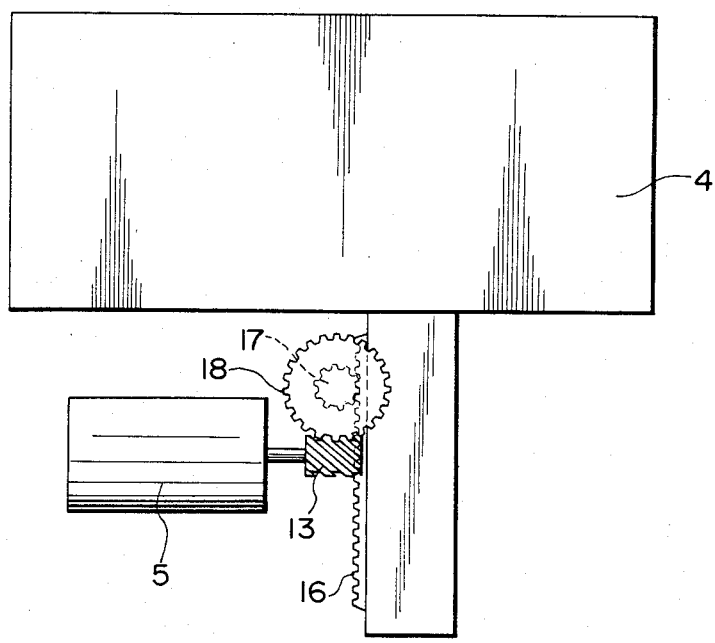
FIG. 7 is a schematic illustration of another example of the mechanism for moving the light-shielding plate up and down.

The described mechanism for driving the light-shielding plate up and down may be modified in a manner shown in FIG. 7. Namely, in this modification, a reference numeral 16 designates a rack which projects by a predetermined distance from the lower or upper edge of the light-shielding plate 4 and meshes with a reduction gear 17. Another reduction gear 18 coaxial with the reduction gear 17 meshes with a pinion 13 on the shaft of the motor 5. In consequence, the rack 16 is moved up and down to vertically drive the light-shielding plate 4 as the motor 5 operates in forward and backward directions.

A reference numeral 19 designates a lead wire to the outer end of which connected is a switch 20 mounted and fixed to the periphery of a switch holder 21. The switch holder 21 is made from a rubber and has a ring-like form for perfectly fitting a finger 26 just like as a ring. The ring-shaped switch holder 21 and the ring 20 mounted on the latter are so constructed that, when the switch holder 21 fits the finger 26, the switch 20 is positioned between the finger 26 and an adjacent finger 27. The ring holder 21 is made from a rubber and is shaped in a perfect endless form to detachably fit the finger 26. When the switch holder fits the finger 26, the switch 20 is positioned to oppose to the side of an adjacent finger 27. The switch holder may be put on the finger of a glove ordinarily used in the welding for protecting the hand from the arc light. For such a way of use, the diameter of the switch holder 21 is somewhat increased to permit a loose fit for facilitating the putting on and off.

Figure 9:
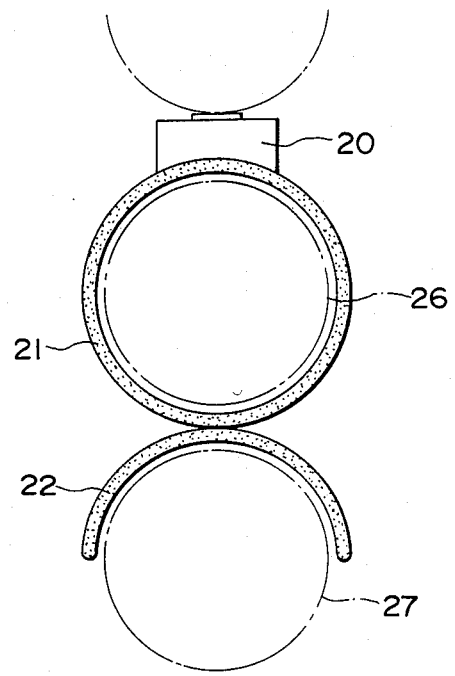
FIG. 9 is an illustration of another embodiment having a modified switch holder.
Figure 10:
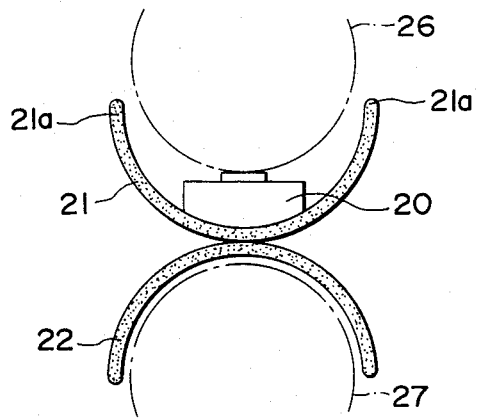
FIG. 10 is an illustration of still another embodiment in which the switch holder is further modified.

FIGS. 9 and 10 show modifications of the switch holder 21. Namely, the switch holder 21 shown in FIG. 9 is provided on its periphery with an arcuate auxiliary piece 22 formed integrally therewith to partially follow the configuration of the adjacent finger 27 to prevent the rotation of the loosely fitted switch holder 21.

The switch holder 21 shown in FIG. 10 has an arcuate ring having both cut ends 21a to fit a part of the periphery of the finger 21 so as to be put between two adjacent fingers. Another arcuate piece serving as the auxiliary piece 22 is attached to the outer periphery of the holder 21 in opposite direction to the latter so as to fit a part of the adjacent finger 27 thereby to prevent easy detaching of the switch holder 21.

Figure 3:
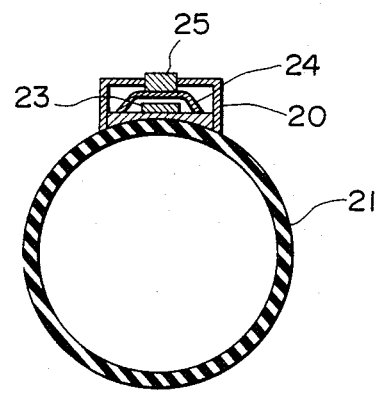
FIG. 3 is a diametrical sectional view of a switch button.

As shown in FIG. 3, the switch 21 has an internal stationary contact piece 23 and a resilient movable contact piece 24 made of a conductive material and disposed above the stationary contact piece 23. A push button 25 is provided above the upper movable contact piece to slightly project from the upper surface of the switch 20 by a small height of, for example, 5 mm so that the switch can be turned on and off by a small depression stroke.

Lead lines (not shown) insulated from each other are connected to the stationary contact piece 23 and the resilient movable contact piece 24, respectively.

In the normal state where no depression force is applied, the resilient movable contact piece 24 is positioned away from the stationary contact piece due to its resiliency so that the switch takes the OFF state.

As the push button 25 is depressed overcoming the force resiliency of the resilient movable contact piece 24, the latter is brought into contact with the stationary contact piece 23 so that the switch is turned ON to electrically connect the aforementioned lead lines to each other.

As the depressing force is removed, the resilient movable contact piece 24 springs back to the initial position to turn the switch off as stated before, so that two lead lines are disconnected from each other.

The switch holder 21 mounting this switch 20 is put on a finger 26 of a hand other that the thumb and the fifth finger. In this state, the push button 25 of the switch 20 makes a slight contact with the side surface of an adjacent finger 27. The pressure exerted on the push button 25 is not increased substantially even when the fingers are folded to create a weak gripping condition.

Figure 8:
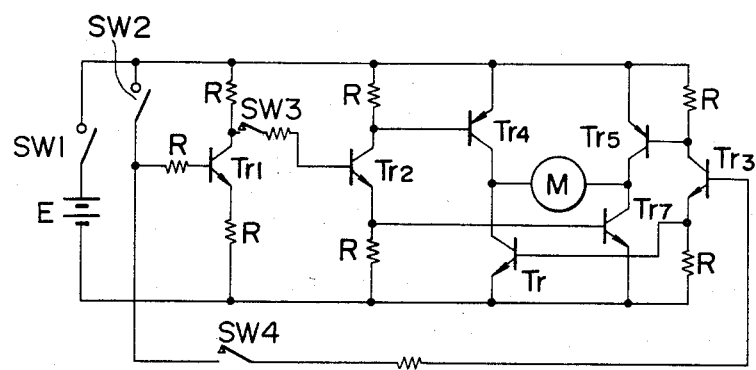
FIG. 8 is an electric circuit diagram.

A typical example of the object to be gripped during the welding is a safety holder which clamps the welding rod. This can be gripped without substantial finger force when the welding is not made. However, when the worker turns to the welding, he grips the safety holder at a greater force. In such a case, the side surfaces or flanks of the two fingers 26,27 are pressed and deformed to apply a high pressure to the push button 25 opposing to the flank of the finger 27, thereby to turn the switch 20 on. In consequence, the mask body electrically connected to the switch 20 makes the following operation by the operation of an electric circuit shown in FIG. 8.

Before the arc is generated, the push button 25 is depressed by the increased gripping force so that transistors $Tr_1$ and $Tr_2$ are turned on while a transistor $Tr_2$ is turned on. In this state, transistors $Tr_4$ and $Tr_7$ takes the on state to cause a forward rotation of the motor 5, so that the guide pin 12 of the rotary disc 4 is swung upward to lift the light-shielding plate 4 to close the window 2 thereby to present a light incoming surface of small light transmission coefficient to shield the eyes of the worker from the arc light.

As the light-shielding plate 4 is moved to the uppermost position, the upper edge thereof comes into contact with the limit switch 14 to close the latter thereby to stop the motor.

Usually, the welding is conducted intermittently with intervals. When the welding is stopped, the grasping force is weakened to release the push button 25. In consequence, transistors $Tr_1$ and $Tr_3$ are turned off, while the transistor $Tr_2$ is turned on. In this state, the transistors $Tr_4$ and $Tr_7$ take off state while the transistors $Tr_5$ and $Tr_6$ take on state to permit the motor 5 to be reversed. In consequence, the guide pin 12 of the rotary disc 6 acts to lower the light-shielding plate 4 to open the window 2. The downward movement of the light-shielding plate 4 is stopped when the latter is moved to the lower limit position to make contact with the limit switch 15.

According to the invention, the light-shielding plate 4 mounted in the protective mask 1 may be substituted by a panel which can generally change its light transmission coefficient electrically, such as an electrochlomic panel or a liquid crystal panel. In such a case, the panel is electrically connected to the switch 20 which is manipulated by hand just before the generation of the arc light to form a light incoming surface of a small light transmission coefficient.

As has been described, according to the invention, it is possible to manipulate the switch by making an effective use of the change in pressure of fingers in accordance with the change in the change in the gripping force. It is, therefore, possible to form the light incoming surface of small light transmission coefficient immediately before the generation of the arc wherever the worker may move, so that the welding work is very much facilitated and the application of arc light to eyes is suppressed without fail to ensure the high safety of the welding work.

What is claimed is:

1. A welder's mask comprising:
   (a) a mask body having a viewing window;
   (b) a light-shielding plate having a low light transmitting coefficient and having dimensions greater than said window, slidably mounted on said mask body for movement between a first position where said plate covers said window and a second position where said plate uncovers said window;
   (c) a motor mounted on said mask body;
   (d) a conversion means mounted on said mask body and connected to said plate and to said motor for moving said plate between said first and second positions;
   (e) a switch holder having an arcuate portion adapted to fit a finger of the welder;
   (f) electric push button switch means having a movable button, said switch being mounted on said holder in position with said button immediately adjacent the side of an adjacent finger of said welder to move to a first position when pressure above a predetermined level is exerted upon said button by said adjacent finger and into a second position when said pressure is reduced below said predetermined level;
   (g) said mask having first electrical switching means operative to rotate said motor in a first direction to activate said conversion means and move said plate into a first position and to stop said motor when said plate moves into said first position when said button is in said first position;
   (h) said mask having second electronic switching means operated to rotate said motor in a second opposite direction to activate said conversion means and move said plate in opposite direction into a second position and to stop said motor when said plate moves into said second position when said button is in said second position; and
   (i) electric lead wire means for connecting said switch to said first and second means for rotating said motor.

2. The mask of claim 1 wherein the switch holder is capable of completely fitting one or more fingers of a user.

3. The mask of claim 1 wherein the switch holder has an arcuate ring portion cut at both ends thereof so as to fit a part of periphery of a finger of a user.

4. The mask of claim 1 wherein the switch holder has an arcuate auxiliary holder piece secured to the outside of said switch holder, said auxiliary holder piece being situated to engage at least the entire side of the periphery of a finger adjacent to the finger of the user, which bears said switch holder, thereby to prevent the rotation of said switch around said finger.

5. The mask of claim 1 wherein the conversion means comprises a gear train operatively connected to the shaft of said motor, a rotary disc fixed to the outermost gear of said gear train, a guide pin projecting from said rotary disc and adapted to move along an arcuate path in accordance with the rotation of said rotary disc, and a guide groove formed in said light-shielding plate which slidingly receives said guide pin.

* * * * *